US00PP22243P2

(12) United States Plant Patent
Qiu et al.

(10) Patent No.: US PP22,243 P2
(45) Date of Patent: Nov. 15, 2011

(54) ROSE PLANT NAMED 'TE QIAO'

(50) Latin Name: *Rosa hybrida*
Varietal Denomination: Te Qiao

(75) Inventors: Bao Ping Qiu, Beijing (CN); Ding Yan Li, Beijing (CN); Zhang Lei, Beijing (CN)

(73) Assignee: Beijing Union University, Beijing (CN)

( * ) Notice: Subject to any disclaimer, the term of this patent is extended or adjusted under 35 U.S.C. 154(b) by 0 days.

(21) Appl. No.: 12/804,228

(22) Filed: Jul. 16, 2010

(51) Int. Cl.
*A01H 5/00* (2006.01)

(52) U.S. Cl. ..... Plt./102; Plt./107

(58) Field of Classification Search ..... Plt./102, Plt./107, 108
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of rose plant named 'Te Qiao', a shrub rose characterized by its upright, compact, densely-branched habit, its semi-glossy green foliage, its red-purple, single flowers, its repeat blooming habit even through hot weather and its vigorous growth with minimal seed production.

2 Drawing Sheets

Botanical classification: *Rosa hybrida.*
Variety denomination: 'Te Qiao'.

CROSS REFERENCE TO A RELATED APPLICATION

This application is co-pending with a U.S. Plant Patent Application filed for a plant derived in the Inventors' breeding program that is entitled Rose Plant Named 'Te Jiao' (U.S. Plant patent application Ser. No. 12/804,238).

BACKGROUND OF THE INVENTION

The present invention relates to a new and distinct cultivar of *Rosa hybrida*. The new cultivar will be referred to hereafter by its cultivar name, 'Te Qiao'. 'Te Qiao' is a shrub rose suitable for landscape plantings.

The new cultivar of shrub rose is a selection from a controlled breeding program conducted by the Inventors in Beijing, China with a focus on creating rose cultivars that perform well and bloom continuously in the hot summers in the northern region of China and also exhibit minimal seed production.

The new variety of shrub rose, 'Te Qiao', arose from a cross made in Beijing, China in 2005 between the female parent, 'Dortmund' (not patented) and the male parent, 'BeilinQiao' (not patented). 'Te Qiao' was selected by the Inventors as a single unique plant from the resulting seedlings in May, 2006.

The new cultivar was first asexually propagated by the Inventors using softwood stem cuttings in Beijing, China in November, 2006. Asexual propagation using stem cuttings and tissue culture has determined that the characteristics of this cultivar are stable and are reproduced true to type in successive generations.

SUMMARY OF THE INVENTION

The following traits have been repeatedly observed and represent the characteristics of the new rose as observed in Beijing, China. These attributes in combination distinguish 'Te Qiao' as a unique cultivar of shrub rose.

1. 'Te Qiao' exhibits single flowers that are bright red-purple in color.
2. 'Te Qiao' blooms continuously from April to November, even through hot summer weather.
3. 'Te Qiao' produces very few to no seeds.
4. 'Te Qiao' exhibits semi-glossy green foliage.
5. 'Te Qiao' exhibits a densely branched, compact, upright shrub habit.
6. 'Te Qiao' exhibits vigorous growth with very good disease resistance.
7. 'Te Qiao' overwinters under natural conditions in Beijing.

The new cultivar of shrub rose can be readily distinguished from its parents. The female parent, 'Dortmund', has a climbing habit, lacks the ability to sustain flower production during hot summer months, and produces red flowers and abundant clusters of fruit. The male parent, 'BeilinQiao', has a shorter stature, produces smaller, pink flowers, numerous seeds, and foliage that is lighter green and non-glossy. 'Te Qiao' can also be most closely compared to a cultivar from the same breeding program, 'Te Jiao', which is similar in its vigor, long blooming habit under hot summer conditions, lack of seed production and disease resistance. 'Te Jiao' differs from 'Te Qiao' in having semi-double pink flowers and in having a climbing growth habit.

BRIEF DESCRIPTION OF THE DRAWING

The accompanying colored photographs illustrate the overall appearance and distinct characteristics of three year-old plants of the new shrub rose, 'Te Qiao', as grown outdoors in a field on its own roots.

DETAILED BOTANICAL DESCRIPTION

Figure 1:
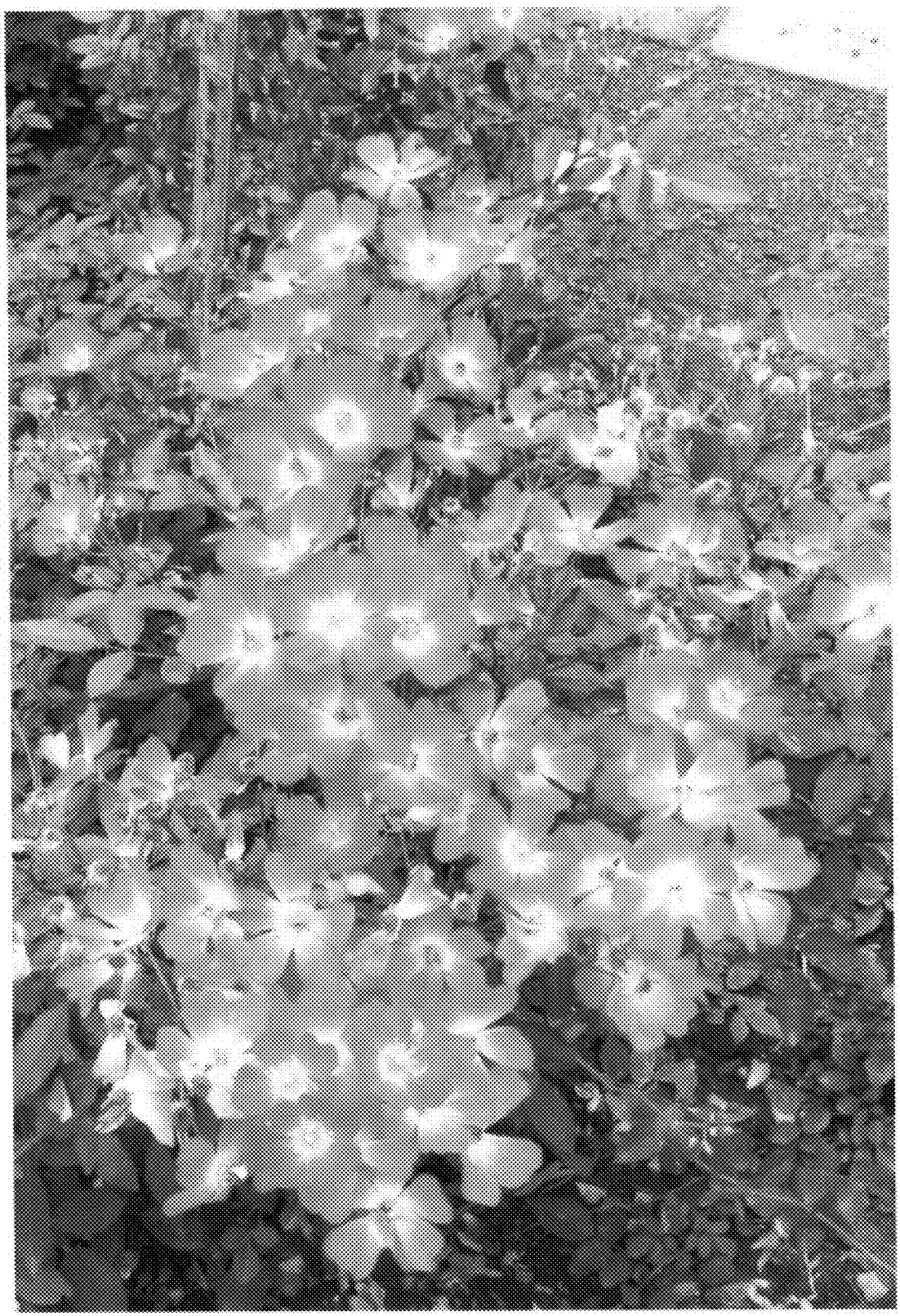
FIG. 1 provides a top view of a plant of 'Te Qiao' and illustrates its flowering habit.
Figure 2:
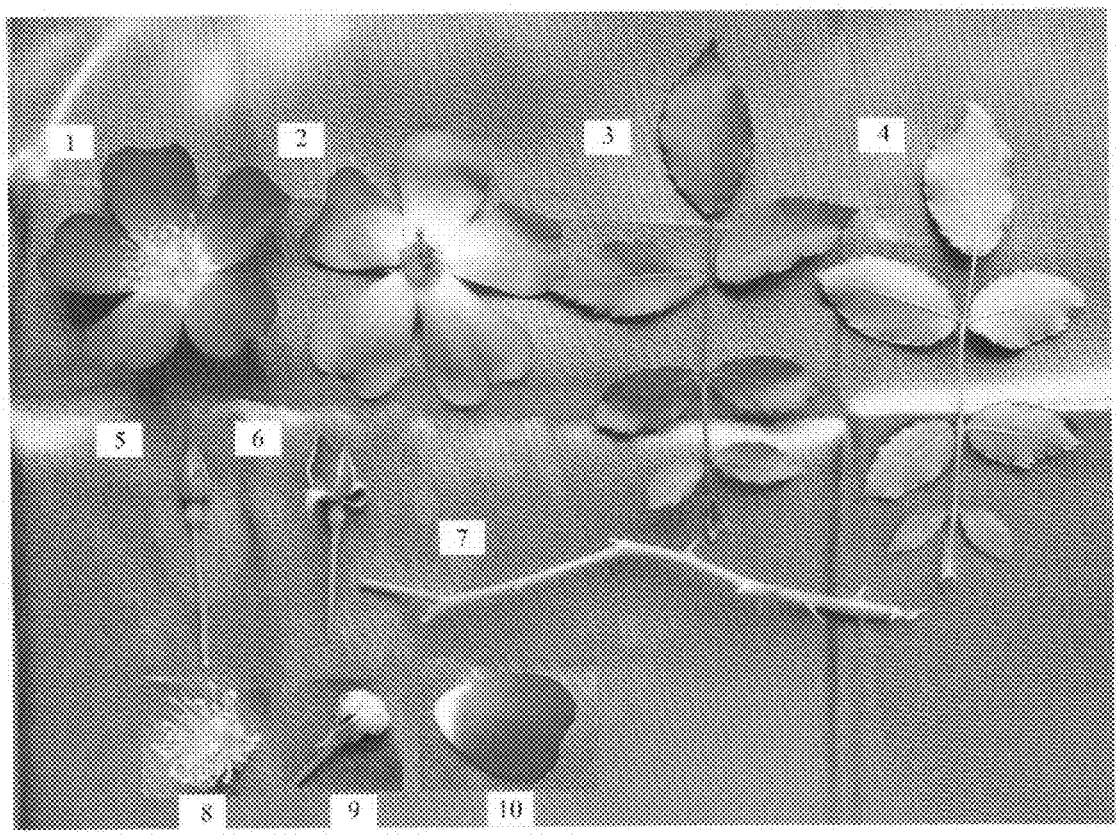
FIG. 2 provides a view of plant parts of 'Te Qiao' with labels; 1: upper surface of flower, 2: lower surface of flower, 3: upper surface of leaf, 4: lower surface of leaf, 5 and 6; flower buds, 7; young stem, 8: reproductive organs, 9: sepals and receptacle, 10; upper surface of petal. The colors in the photographs are as close as possible with digital photography techniques available, the color values cited in the detailed botanical description accurately describe the colors of the new shrub rose.

The following is a detailed description of the new cultivar as observed on 3 year-old plants as field grown in Beijing, China. Growing conditions had an average temperature of 25.8 to 24.4° C. with temperatures ranging between 12.3 and 39.6° C. and average precipitation during the months of July and August of 196.6 to 243.5 mm. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming habit.*—Repeat blooming from last week of April to mid November.

*Plant habit.*—Shrub, upright, densely branched, compact.

*Height and spread.*—Averaging 0.7 to 1 m in height and 1 m in spread.

*Cold hardiness.*—Can be overwintered under natural conditions in Beijing, China.

*Diseases and pests.*—Good resistance to fungal disease. Pest resistance and susceptibility have not been observed.

*Propagation.*—Stem cuttings and tissue culture.

*Growth rate.*—Vigorous.

Branch description:

*Stem color.*—Young and maturing; 144C suffused with 183D, mature wood; 146A.

*Stem surface.*—Smooth, semi-glossy on new growth.

*Stem size.*—Average of 4 mm in width, up to 40 cm in length.

*Internode.*—Average of 5 cm.

*Thorns.*—12 per 10 cm of stem, 8 to 10 mm in length, 150C suffused with 183D, present on new growth.

Foliage description:

*Leaves.*—Division is odd-pinnate, arrangement is alternate, average of 13.0 cm in length and 8.0 cm in width.

*Leaflets.*—Ranging from 3 to 7, most frequently 7, elliptic in shape, obtuse base, acuminate apex, ciliate margins, weakly crenulate, upper surface and lower surface semi-glossy and glabrous, average of 5.0 cm in length and 2.5 cm in width, color: young upper surface; 144A, young lower surface: 145A, mature upper surface; 139A, mature lower surface; 138B.

*Venation.*—Pinnate, 183D in color on upper and lower surface.

*Rachis.*—Average of 8 cm in length and 1 to 1.5 mm in diameter, surface smooth, color 138A suffused with 183D on younger growth.

*Stipules.*—Broad base, curved inwards at point of attachment, bifid apex, average of 15 mm in length and 10 mm in width, color on upper side is 138A suffused with 183D on the center of stipule, margins ciliate and crenulate.

*Petioles.*—Average of 1 mm in length and 1 mm in diameter, surface glabrous, upper surface 139A suffused with 183D in color, lower surface 137B.

Inflorescence description:

*Inflorescence type.*—Typically corymbs of 3 to 7 single flowers.

*Flower number.*—4 to 19 flowers per lateral stem.

*Flower fragrance.*—Moderately scented.

*Flower longevity on the plant.*—About 3 to 5 days, persistent.

*Flower type.*—Semi-double, round, held upright.

*Flower size.*—Average of 6 to 7 cm in diameter and 2 cm in depth.

*Peduncles.*—Upright, an average of 3.0 cm in length and 1.0 cm in diameter, glabrous to sparsely pubescent surface, 138A in color.

*Bracts.*—None observed.

*Flower buds.*—Narrowly ovate in shape, an average of 2.5 cm in length and 1.0 cm in width prior to opening, 59D in color.

*Sepals.*—6, lanceolate in shape, margins weakly foliaceous appendages on 3 of the 6 sepals and stipitate glands, average of 2.1 cm in length and 0.6 mm in width, acute apex, truncate base fused with receptacle, upper surface tomentose and 134C in color, lower surface glabrous and 134B in color.

*Petals.*—5 per flower, drop readily and cleanly, obcordate in shape, upper and lower surface smooth, margin crenulate, base broadly cuneate in shape, apex is rounded with indented notch, average of 3.5 cm in length and 2.5 cm in width, color: opening flowers upper surface; blend of 57A and 67A suffused with 155D extending irregularly into the middle region from petal spot, petal spot 155D, opening flowers lower surface; a blend of 57A and 67C suffused with 155D extending irregularly into the middle region from petal spot, petal spot 155D, fully open flowers upper surface; a blend of 57B and 67B suffused with 155D extending irregularly into the middle region from petal spot, petal spot 155D, lower surface; a blend of 57C and 67C suffused with 155D extending irregularly into the middle region from petal spot, petal spot 155D, color when fading upper and lower surface; 68D and 68C.

*Receptacle.*—Average of 5 mm in diameter and 6 mm in depth when flower is fully open, urned-shaped, glabrous surface, 149C in color.

*Pistils.*—About 30 per flower, 3 mm in length, stigma is an average of 1 mm in length and 0.4 mm in width and 158B in color, style is an average of 7 mm in length and 158C in color, ovary is oblong in shape and 144C in color.

*Stamens.*—About 100 per flower, filaments are about 5 to 10 mm in length and 55C in color, anthers are an average of 2.0 mm in length and 12B in color, pollen is moderate in quantity and near 12C in color.

*Hips.*—None were observed to form to date prior to the frost date in Beijing, China.

It is claimed:

1. A new and distinct cultivar of rose plant named 'Te Qiao' as herein illustrated and described.

* * * * *

UNITED STATES PATENT AND TRADEMARK OFFICE

CERTIFICATE OF CORRECTION

PATENT NO. : PP22,243 P2
APPLICATION NO. : 12/804228
DATED : November 15, 2011
INVENTOR(S) : Ping Qui Bao, Yan Li Ding and Lei Zhang It is certified that error appears in the above-identified patent and that said Letters Patent is hereby corrected as shown below:

Title Page, item (75);

Incorrect format of Inventor's names:

Qui; Bao Ping (Beijing, CN), Li; Ding Yan (Beijing, CN), Lei; Zhang (Beijing, CN)

Corrected format of Inventor's names:

Bao; Ping Qui (Beijing, CN), Ding; Yan Li (Beijing, CN), Zhang; Lei (Beijing, CN)

Signed and Sealed this
Twenty-second Day of May, 2012

David J. Kappos

David J. Kappos
*Director of the United States Patent and Trademark Office*